United States Patent [19]
Wong et al.

[11] Patent Number: 5,601,079
[45] Date of Patent: *Feb. 11, 1997

[54] NON-INVASIVE QUANTIFICATION OF GLUCOSE CONTROL, AGING, AND ADVANCED MAILLARD PRODUCTS BY STIMULATED FLUORESCENCE

[76] Inventors: Jacob Y. Wong, 4589 Camino Molinero, Santa Barbara, Calif. 93110; Bent Formby, 1625 Overlook La., Santa Barbara, Calif. 93103; Charles M. Peterson, 1075 San Antonio Creek Rd., Santa Barbara, Calif. 93111

[*] Notice: The term of this patent shall not extend beyond the expiration date of Pat. No. 5,370,114.

[21] Appl. No.: 307,125

[22] Filed: Sep. 16, 1994

Related U.S. Application Data

[63] Continuation-in-part of Ser. No. 852,085, Mar. 12, 1992, Pat. No. 5,370,114.

[51] Int. Cl.⁶ .................................................. A61B 6/00
[52] U.S. Cl. ......................... 128/633; 128/665; 356/39
[58] Field of Search .................................. 128/633, 665; 356/39, 40, 41

[56] References Cited

U.S. PATENT DOCUMENTS

| | | | |
|---|---|---|---|
| 4,556,057 | 12/1985 | Hiruma et al. | 128/633 |
| 4,894,547 | 1/1990 | Leffell et al. | 128/633 |
| 4,957,114 | 9/1990 | Zeng et al. | 128/665 |
| 4,981,138 | 1/1991 | Deckelbaum et al. | 128/665 |
| 5,341,805 | 8/1994 | Stavridi et al. | 128/633 |
| 5,348,018 | 9/1994 | Alfano et al. | 128/665 |
| 5,370,114 | 12/1994 | Wong et al. | 128/633 |

*Primary Examiner*—Angela D. Sykes
*Assistant Examiner*—Eric F. Winakur
*Attorney, Agent, or Firm*—Lyon & Lyon

[57] ABSTRACT

An apparatus for measuring the concentration of selected solute in a solution. This apparatus is particulary suitable for measuring the concentration of blood components, such as blood late Maillard products. A beam of exposing light is imaged through a wall of a containment vessel onto a region of the sample adjacent to this wall to induce from said selected solute emission of light that includes at least one emission peak that can be used to calculate the concentration of this solute. At least one detector is positioned to maximize the strength of detected signal, if other components of this solution strongly absorb the emitted light. The exposing light is directed such that the detected signal is maximized as a function of the path of this exposing light. A particular embodiment is a low-cost, non-invasive blood Maillard products concentration detector. In this embodiment, the containment vessel is preferably one of the patient's fingers. At least two additional detected signals are monitored and processed at wavenumbers suitable for eliminating temperatures and pressure effects on the calculated blood glucose levels.

18 Claims, 9 Drawing Sheets

NON-INVASIVE QUANTIFICATION OF GLUCOSE CONTROL, AGING, AND ADVANCED MAILLARD PRODUCTS BY STIMULATED FLUORESCENCE

RELATED APPLICATION

This application is a continuation-in-part of application Ser. No. 07/852,085, filed Mar. 12, 1992, now U.S. Pat. No. 5,370,114, entitled "Blood Chemistry Measurement By Stimulated Infrared Emission", the disclosure of which is specifically incorporated herein by reference.

BACKGROUND OF THE INVENTION

1. Field of the Invention

The present invention is in the field of medical instrumentation. More specifically it relates to a small and portable sensor capable of making non-invasive measurements of average glucose levels and the aging process over time by quantifying fluorescent chemical molecular species in blood and tissue.

2. The Prior Art

An estimated 14 million Americans have diabetes mellitus with comparable prevalence rates in the rest of the world. The recently completed Diabetes Control and Complications Trial sponsored by the National Institutes of Health has confirmed that good glucose control over time can influence positively several outcome variables in this disease including blindness and kidney failure (Report: Diabetes Control and Complications Trial (DCCT) Summary and Recommendations reported at the 53rd Annual Meeting of the American Diabetes Association Jun. 12–15, 1993 Las Vegas, Nevada). Thus providing useful measures of glucose control and creating programs that enable persons with diabetes to control the illness have taken on even greater importance.

At the present there are two general methods by which glucose control can be quantified over time: self blood glucose monitoring by the individual subject and measurement of glycosylated proteins. Both of these approaches require a sample of blood. Home blood glucose monitoring provides information regarding the blood glucose at the moment and allows immediate correction of metabolic problems. Measurement of glycosylated or glycated proteins allows the quantification of glucose control over a longer period of time such that the overall efficacy of a management strategy can be determined. The DCCT utilized both approaches.

Measurement of glycated proteins has primarily used hemoglobin because it is easily obtained and because there is no new synthesis of hemoglobin in the red cell after three days in the circulation. Therefore whatever glycation occurs must be the result of a postsynthetic (post-translational) reaction and reflect the metabolic environment to which the hemoglobin has been exposed. The 120 day lifespan of the red cell allows the retrospective quantification of average glucose levels over time. The art of separating minor hemoglobins will be reviewed in some detail since it pertains to the present invention. In addition, the same chemical process has been shown to occur with other proteins in the body and proceed to the generation of fluorescent species known as advanced Maillard reaction products or nonenzymatic browning products or melanoidins which comprise the subject of measurement of the present invention.

The documentation that there is nonenzymatic post translational modification of proteins by sugars (glycation) has provided clinicians with a measurement of glucose control and investigators with a testable hypothesis regarding the biochemical basis for a number of pathological consequences of hyperglycemia. While the latter remains an hypothesis, the former has become fixed in the clinical equipment and methods used especially in medicine.

Studies in the clinical literature prior to the advent of measurements of glycated proteins remain difficult to interpret and controversial, in part because of the confounding influence of lack of documentation of "glucose control". Claims of "good control" versus "bad control" unencumbered by objective evidence produced more heat than light in the field of diabetes until the clinical availability of glycosylated or glycated hemoglobin assays.

Just as it is difficult to interpret clinical studies in diabetes without evidence of "control" as reflected by a well performed assay of glycation, so it is difficult to judge the level of clinical care in a given patient without such a measurement performed at intervals which allow evaluation of ongoing glycemia. Any assessment of care for patients with diabetes has to include glycemia as reflected by such an assay. The goal of modern diabetes management has become reestablishment of the normal internal milieu while avoiding hypoglycemia. Therefore, every clinician needs to be familiar with the glycosylation assay provided by his/her laboratory and be able to interpret the results in depth to the patient.

2.1 Separation of hemoglobin variants

The study of hemoglobin variants has provided a number of significant medical insights. In 1949, Linus Pauling and coworkers analyzed hemolysates by moving boundary electrophoresis and found that the hemoglobin from a patient with sickle cell anemia had a different mobility from that of a normal individual. This experiment provided the first identification of a "molecular disease". Pauling L, Itano H, Singer SJ, and Wells IC: Sickle cell anemia: A molecular disease. *Science* 1949; 110:543–4.

In normal human erythrocytes, hemoglobin A (Hb A or $A_0$) comprises about 90 percent of the total hemoglobin. Besides Hb A, human red cells contain other hemoglobin components that are of considerable interest. Some of these, such as Hbs $A_2$ and F, like sickle hemoglobin (Hb S) are products of alternate globin chain genes, and others such as $HbA_{1c}$ are post-translational modifications of Hb A.

In 1955, Kunkel and Wallenius analyzed human hemolysates by starch gel electrophoresis and found a minor component that had less negative charge than HbA and comprised about 2.5% of the total. This component was designated Hb A2 with two alpha and two a chains and was found to be elevated in individuals with 3 thalassemia. Kunkel HG and Wallensius G: New hemoglobins in normal adult blood. *Science* 1955; 122:228–9. Kunkel HG, Ceppellini R, Muller-Eberhard U, Wolf J: Observations on the minor basic hemoglobin components in the blood of normal individuals and patients with thalassemia. *J Clin Invest* 1961:36:1615–21. They also noted several hemoglobin species which had more negative charge, one of which was undoubtably Hb $A_{1c}$. As early as 1958, Allen and coworkers noted that human hemoglobin could be separated into at least 3 minor components using column chromatography. Allen DW, Schroeder WA, Balog J: Observations on the chromatographic heterogeneity of normal adult and fetal human hemoglobin. *J Am Chem Soc* 1958:80:1628–34. The minor components were labelled in order of their elution from the column; hence, hemoglobins $A_{1a}$, $A_{1b}$, $A_{1c}$.

During the 1960's it was demonstrated that a hexose molecule attaches to the hemoglobin structure in the fast eluting components. Holmquist WR, Schroeder WA: A new N-terminal blocking group involving a Schiff base in hemoglobin $A_{1c}$. *Biochemistry* 1966;5: 2489–2503. Bookchin RM, Gallop PM: Structure of hemoglobin Alc: Nature of the N-terminal beta chain blocking group. *Biochim Biophys Res Commun* 1968;32:86–93. In 1962 Huismann and Dozy using gel electrophoresis found an increased level of minor hemoglobin components in a few diabetic patients treated with tolbutamide. Huisman THJ, Dozy AM: Studies on the heterogeneity of hemoglobin. V. Binding of hemoglobin with oxidized glutathione. *J. Lab Clin Med* 1962;60: 302–19. However, this finding remained unheeded until Rahbar, also using gel electrophoresis, re-discovered the existence of an elevation in these minor fractions in two patients with diabetes mellitus and later confirmed the observation in 140 diabetic patients. Rahbar S: An abnormal hemoglobin in red cells of diabetics. *Clin Chem Acta* 1968; 22:296–8. Rahbar S, Blumenfeld O, Ranney HM: Studies of an unusual hemoglobin in patients with diabetes mellitus. *Biochem Biophys Res Commun* 1969; 36:838–43. Trivelli et al (using the column cation exchange chromatographic method which became standard) found that in persons with diabetes mellitus, the concentration of Hb $A_{1c}$ was 2–3 times higher than in non-diabetic individuals. Trivelli LA, Ranney HM, Lai H-T: Hemoglobin components in patients with diabetes mellitus. *N Eng J Med* 1971; 248:353–7. In 1975 Tattersall et al studied a series of monozygotic twins of whom only one had diabetes and found elevated Hb $A_{1c}$ levels in the diabetic twins only. Because of a low correlation with fasting plasma glucose levels, they concluded that the measurement did not correlate with glycemia per se. Tatersall RB, Pyke DA, Ranney HM, Bruckheimer SM: Hemoglobin components in diabetes mellitus: Studies in identical twins. *N Engl J Med* 1975; 293: 117103.

In 1976, it became clear that Hb $A_{1c}$ resulted from a post translational modification of hemoglobin A by glucose and that there was a clinical relationship between Hb $A_{1c}$ and fasting plasma glucose, peak on the glucose tolerance test, area under curve of the glucose tolerance test, and mean glucose levels over the preceding weeks. Bunn HF, Haney Dn, Kamin S, Gabbay KH, Gallop PM. The biosynthesis of human hemoglobin $A_{1c}$. *J Clin Invest*–57:1652-9. Koenig RJ, Peterson CM, Kilo C, Cerami A, Williamson JR: Hemoglobin $A_{1c}$ as an indicator of the degree of glucose intolerance in diabetes. *Diabetes* 1976; 25:230–232. Koenig RJ, Peterson CM, Jones RL, Saudek CD, Lehrman M, Cerami A: Correlation of glucose regulation and hemoglobin $A_{1c}$ in diabetes mellitus. *N Engl J Med* 1976; 295:417–20. It soon became apparent that an improvement in ambient blood glucose levels resulted in correction (inter alia) of Hb $A_{1c}$ levels (Peterson CM, Jones RL, Koenig RJ, Melvin ET, Lehrman ML: Reversible hematologic sequelae of diabetes mellitus. *Ann Int Med* 1977; 86:425–429. Peterson CM, Koenig RK, Jones RL, Saudek CD, Cerami A: Correlation of serum triglyceride levels and hemoglobin $A_{1c}$ concentrations in diabetes mellitus. *Diabetes* 1977; 26:507–9) and that these nonenzymatic glycosylation reactions might provide an hypothesis which could explain a number of the pathological sequelae of diabetes mellitus via toxicity arising from glucose adduct formation with proteins or nucleic acids. Peterson CM, Jones RL: Minor hemoglobins, diabetic "control" and diseases of postsynthetic protein modification. *Ann Int Med* 1977; 87: 489–91.

2.2 Chemistry of glucose adduct formation

As early as 1912, Maillard suggested that the chemical reactions that now bear his name might play a role in the pathology associated with diabetes mellitus. Maillard LC: Reaction generale des acides amines sur les sucres; ses consequences biologiques. *C.R. Acad Sci* 1912; 154:66–68. The ability of reducing sugars to react with the amino groups of proteins is now widely recognized as is the natural occurrence of many nonenzymatically glycosylated proteins. Important details as to the nature of such reactions are, however, still unclear.

The initial step (or Early Maillard Reaction) involves the condensation of an amino moiety with the aldehyde form of a particular sugar. Only a very small fraction of most common sugars is normally present in the aldehyde form (Table 1). Angyal SJ: The composition of reducing sugars in solution, in Harmon RE (ed): *Asyummetry in Carbohydrates*. New York, Marcel Dekker, 1979, pp 15–30. Benkovic SJ: Anomeric specificity of carbohydrate utilizing enzymes. *Methods Enzymol* 1979; 63:370–9. A number of transformations are possible following the addition of an amine to a sugar carbonyl group. Considerable evidence now exists which supports the involvement of an Amadori-type rearrangement for the adduct of glucose with the N-terminus of the B-chain of hemoglobin. The labile Schiff base aidimine adduct is transformed to a relatively stable ketoamine adduct via the Amadori Rearrangement.

TABLE 1

| % OF SUGARS IN ALDEHYDE FORM | |
|---|---|
| Glucose | 0.001 |
| Ribose | 0.017 |
| Fructose | 0.25 |
| Glucose 6-P | 0.4 |
| Fructose 6-P | 4–5 |

Since hemoglobin circulates in its red cell for approximately 120 days, there is some opportunity in this cell for Late Maillard Reactions or enzymatic browning to occur. In these late Maillard Reactions, the Amadori product is degraded into deoxyglucosones which react again with free amino groups to form chromophores, fluorophores, and protein cross links. Hayase F, Nagaraj RH, Miyata S, Njoroge FG, Monnier VM: Aging of proteins: immunological detection of a glucose-derived pyrrole formed during Maillard Reaction in vivo. *J Biol Chem* 1989; 263:3758–3764. Peterson CM (ed): *Proceedings of a conference on Nonenzymatic Glycosylation and Browning Reactions: Their Relevance to Diabetes, Mellitus. Diabetes* 1982; 31 (Suppl 3) 1–82. In tissues which are longer lived, these reactions may be important mediators of diabetes pathology as well as the aging process. Although the structure of a large number of nonenzymatic browning products has been elucidated, few have been obtained under physiological conditions, thus making detection in vivo difficult and their pathological role uncertain. Horiuchi S, Shiga M, Araki N, Takata K, Saitch M, Morino Y: Evidence against in vivo presence of 2-(2-furoyl)-4(B)-(2-furanyl)1H-imidazole, a major fluorescent advanced end product generated by nonenzymatic glycosylation. *J Biol Chem* 1988;263:18821–6.

Table 2 summarizes the hypotheses whereby Maillard Reactions might contribute to the multiple pathologies associated with hyperglycemia. Peterson CM, Formby B: Glycosylated proteins, in Alberti KGMM, Krall LP (eds): *Diabetes Annual* 1 , New York, Elsevier, 1985, pp 1781 97. Peterson CM, Formby B: Glycosylated Proteins, in Alberti KGMM Krall LP (eds): *Diabetes Annual* 2. New York, Elsevier, 1986, pp 137–155. Kowluru RA, Heidorn DB, Edmondson SP, Bitensky MW, Kowluru A, Downer NW, Whaley TW, Trewhella J: Glycation of calmodulin: Chemistry and structural and functional consequences. *Biochem.*

1989; 28:2220–8. Arai K, Maguchi S, Fujii S, Ishibashi H, Oikawa K, Taniguchi N: Glycation and inactivation of human Cu-Zn-superoxide dismutase. Identification of the in vitro glycated sites. *J Biol Chem* 1987;262: 16969–78. Kaneshige H: Nonenzymatic glycosylation of serum IgG and its effect on antibody activity in patients with diabetes mellitus. *Diabetes* 1987; 36:822–8. In addition to the numerous studies of Early Maillard Reactions, the Late Maillard Reactions have been shown to increase concomitantly with diabetes related pathologies. Brownlee M, Cerami A, Vlassara H: Advanced products of nonenzymatic glycosylation and the pathogenesis of diabetic vascular disease. *Diabetes Metab Rev.* 1988; 4: 437–51. Monnier VM, Sell DR, Abdul Karim FW, Emancipator SN: Collagen browning and cross-linking are increased in chronic experimental hyperglycemia. Relevance to diabetes and aging. *Diabetes* 37:86772. Cohen MP: *Diabetes and Protein Glycosylation: Measurement and Biologic Relevance.* New York, Springer-Verlag, 1986. McCance DR, Dyer DB, Dunn JA, Bailie KE, Thorpe SR, Baynes JW, Lyons TJ. Maillard reaction products and their relation to complications in insulin-dependent diabetes mellitus. J. Clin. Invest. 91: 2470–2478, 1993. It remains difficult to establish whether these glycosylation changes are indeed causal of pathology associated with diabetes mellitus. J. Clin. Invest. 91: 2470–2478, 1993.

TABLE 2

Hypotheses regarding the potential role of non-enzymatic glucosylation and browning in the pathology associated with diabetes mellitus I Structural proteins
   A   Collagen: Decreased turnover, flexibility, solubility; increased aggregating potential for platelets, binding of immunoglobulins, crosslinking, and immunogenicity
   B   Lens crystallins and membrane: opacification, increased vulnerability to oxidative stress
   C   Basement membrane: increased permeability, decreased turnover, increased thickness
   D   Extracellular matrix: changes in binding to other proteins
   E   Hemoglobin: change in oxygen binding
   F   Fibrin: decreased enzymatic degradation
   G   Red cell membrane: increased rigidity
   H   Tubulin: cell structure and transport
   I   Myelin: altered structure and immunologic recognition
II Carrier proteins
   A   Lipoproteins: alternate degradative pathways and metabolism by macrophages and endothelial cells, increased immunogenicity
   B   Albumin: alteration in binding properties for drugs and in handling by the kidney
   C   Ig G: Altered binding
III Enzyme systems
   A   Cu—Zn Superoxide Dismutace
   B   Fibrinogen: altered coagulation
   C   Antithrombin III: hypercoagulable state
   D   Purine nucleoside phosphorylase: aging of erythrocytes
   E   Alcohol dehydrogenase: substrate metabolism
   F   Ribonuclease A: lose of activity
   G   Cathepsin B: loss of activity
   H   N-acetyl-D-glucosaminidase: loss of activity
   I   Calmodulin: decreased calcium binding
IV Nucleic acids
   Age-related changes, congenital malformations
V Potentiation of other diseases of post-synthetic protein modification
   A   Carbamylation-associated pathology in uremia
   B   Steroid cataract formation
   C   Acetaldehyde-induced changes in alcoholism 2.3 Terminology, pros, and cons of various measurements Table 3 summarizes terminology used for hemoglobin which has been reacted with sugars.

TABLE 3

Hemoglobin (Hb) Terminology

"Fast" Hemoglobin. The total $HbA_1$ fractions ($HbA_{1a}$, $HbA_{1a2}$, $HbA_{1b}$, $HbA_{1c}$) which, because of more negative charge, migrates toward the anode on electrophoresis and elutes earlier on cation exchange chromatography than $HbA_c$.
Fetal Hemoglobin (HbF). The major hemoglobin component of newborn blood. HbF co-elutes with $HbA_{1c}$ by column chromatography.
Glucosylated Hemoglobin. Hemoglobin modified by glucose at beta chain valine residues and epsilon amino groups of lysine residues.
Glycated Hemoglobin. A term favored by biochemists to indicate adducts of sugars and hemoglobin which are formed non-enzymatically.
Glycosylated Hemoglobin (glyco-hemoglobin). A generic term for hemoglobin containing glucose and/or other carbohydrate at either valine or lysine residues thus the sum of glycosyl adducts.
Hemoglobin A. The major adult form of hemoglobin. A tetramer consisting of two alpha and two beta chains (alpha$_2$, beta$_2$).
Hemoglobin $A_c$. The major component of HbA identified by its chromatographic and electrophoretic properties. Post-translational modifications, including glycosylation do exist, but do not significantly affect the charged properties of the protein.
Hemoglobin $A_1$. Post-translationally modified, more negatively charged forms of $HbA_c$ (primarily glycosylation at the beta chain terminal valine residue) separable from $HbA_c$ by chromatographic and electrophoretic methods.
Hemoglobin $A_{1a1}$, $HbA_{1a2}$, $HbA_{1b}$, $HbA_{1c}$. Chromatographically distinct stable components of $HbA_1$.
Hemoglobin $A1_{1a1}$, $HbA_{1a2}$, $HbA_{1b}$: "Fastest" most anionic forms of HbA consisting primarily of adducts of phosphorylated glycoyltic intermediates with $HbA_c$.
Hemoglobin $A1_c$. Component of $HbA_1$ which consists of 50 to 90% hemoglobin (depending on the quality of resolution of the chromatographic system) glucosylated by a ketamine linkage at the beta chain terminal valine residue.
Pre-Hemglobin $A_{1c}$. A labile form of glycosylated Hb containing glucose bound in aldimin linkage to the beta chain terminal valine residue.
Hemoglobin-AGE. Advanced Maillard or glycosylation end products bound to hemoglobin. Circulate in the red cell and correlates with the amount of hemoglobin $A_{1c}$.

$HbA_{1c}$ is one of several minor hemoglobins, but because of its relatively high concentration in normal persons (3% to 6% of normal hemoglobin), it is the one most extensively studied. Because circulating red blood cells or erythrocytes are incapable of initiating protein synthesis, $HbA_{1c}$ is produced as a post-synthetic modification of hemoglobin $A_0$ (or adult hemoglobin). The rate of modification depends on the mean circulating sugar (glucose) levels to which the erythrocyte is exposed. The post-synthetic modification of hemoglobin A to form $HbA_{1c}$ is nearly irreversible, and its rate of synthesis reflects the glucose environment in which the erythrocyte circulates. Hemoglobin $A_1$ is a descriptive term which describes all the fast hemoglobins which include $HbA_{1c}$ as well as $HbA_{1a}$ and $HbA_{1b}$. Because many of these hemoglobins have glucose or glucose breakdown products (phosphorylated glycolytic intermediates) attached, they are referred to as glycosylated hemoglobins and also reflect average glucose over time; however, the value for glycosylated hemoglobins is about 50% higher than the measurement of $HbA_{1c}$ (or glucosylated hemoglobin) alone.

Table 4 summarizes the available clinical methods of measurement for circulating glycated proteins and the relative benefits and disadvantages of each method. Today a number of $HbA_{1c}$ column methods are available in addition to new radioimmunoassay methods, isoelectric focusing methods, and calorimetric methods. This later measurement can be performed on a spot of capillary blood placed on a filter paper shipped to a central laboratory. One can obtain a glycohemoglobin or glycated serum protein measurement by sending the sample to any one of a number of commercial laboratories. Fructosamine assays of serum proteins have become popular because they are amenable to automation; however, they have the major disadvantage of being influenced by ingested oxidants and reductants thus leading to considerable intraindividual variation not related to glycemia.

TABLE 4

Classification of Current Clinical Assays

I. Physical methods based on changes in pI
  A. Cation exchange chromatography
    PRO: Inexpensive and rapid
    CON: Sensitive to small changes in resin packing, ionic strength, pH, temperature, column loading, and affected by the labile fraction. Variant hemoglobins may interfere.
  B. High performance liquid chromatography (HPLC)
    PRO: Dedicated instruments avoid many problems in 1
    CON: Relatively expensive
  C. Agarose gel eletrophoresis
    PRO: Inexpensive, minimal technician time, standardized plates and conditions in kits less sensitive to pH, triglyceride concentrations, and temperature
    CON: Precision problems induced by scanner and loading variation; sensitive to liabile fraction and variant hemoglobin.
  D. Isoelectric focusing
    PRO: Separates most minor hemoglobin variants
    CON: Precision over time dependent on use of same batch of ampholines on standardized plates; scanning effects precision
II. Methods based on chemical principles
  A. Thiobarbituric acid/colorimetric assay
    PRO: Minimally effected by storage condition, fructose or 5-hydroxy-methyl furfural standards may be incorporated, filter paper assays available
    CON: Difficult to establish, large amount of technical time required, and affected by labile fraction
  B. Affinity chromatography with immobilized m-phenylboronate
    PRO: Rapid, inexpensive, minimally effected by chromatographic conditions, eliminates labile adduct
    CON: Resins vary within and between manufacturers
  C. Fructosamine determination by nitroblue tetrazolium reduction
    PRO: Inexpensive, standards incorporated, may be automated, not effected by labile adduct
    CON: Only for serum, lipids may interfere, reducing substances (in diet) may interfere
III. Immunoassay
    PRO: Inexpensive, rapid, sensitive, specific, not effected by labile adduct
    CON: Antibodies difficult to raise As noted above, in 1912, Louis Camille Maillard at the Sorbonne reported that aqueous solutions of reducing sugars turned progressively yellow-brown when heated or when stored under physiological conditions. Maillard LC: Reaction generale des acides amines sur les sucres; ses consequences biologiques. C.R. *Acad Sci* 1912; 154:66–68. For the next 60 years progress in understanding Maillard's reaction was largely restricted to the food industry. These fluorescent compounds were found to influence the flavor, taste, consistency, and overall appeal of foods as well as their nutritive properties. Kaanane A and Lubuza TP The Maillard Reaction in foods. In Baynes JW and Monnier VM (1989)The Maillard Reaction in Aging, Diabetes, and Nutrition. Alan R. Liss, New York, pp 301–328.

These fluorescent species can be found in vivo as well although a chemical assignment for the species involved is generally lacking. Evidence for the occurrence of the advanced Maillard reaction in long-lived molecules has been based in part on the presence of fluorescence that can be duplicated by incubation of proteins with glucose. Monnier VM, Kohm RR, Cerami A (1984). Accelerated age-related browning of human collagen in diabetes mellitus. Proc Natl Acad USA 81:853–857. Monnier VM, Vishwanath B, Frank KE, Elmets CA, Dauchot P, Kohn RR (1986). Relation between complications of Type I diabetes mellitus and collagen-linked fluorescence. N Engl J Med 314: 403408. Borohydride reducible as well as fluorescent products that co-chromatograph with similar molecules isolated from glucose-incubated proteins have been detected in lens and collagen. Monnier VM, Cerami A (1983). Nonenzymatic glycosylation and browning of proteins in vivo. In The Maillard Reaction in Foods and Nutrition, Waller GR and Feather MS Eds, American Chemical Society, Symposium Series 215:431–449. Oimomi M, Maeda Y, Hata F, Kitamura Y, Matsumoto S, Baba S, lga T, Yamamoto M (1988). Glycation of cataractous lens in nondiabetic senile subjects and in diabetic patients. Exp Eye Res 46:415–420. Further studies on the nature of the fluorophores that accumulate in aging human collagen revealed the presence of two major fluorophores with excitation-emission maxima at 328/378 nm, 335/385 nm and 360/460 nm respectively. McCance DR, Dyer DB, Dunn JA, Bailie KE, Thorpe SR, Baynes JW, Lyons TJ. Maillard reaction products and their relation to complications in insulin-dependent diabetes mellitus. J. Clin. Invest. 91: 2470–2478, 1993. Monnier VM. Toward a Maillard Reaction theory of aging. In Baynes JW and Monnier VM (1989) The Maillard Reaction in Aging, Diabetes, and Nutrition. Alan R. Liss, New York, pp1–21. Dyer DG, Dunn JA, Thorpe SR, Bailie KE, Lyons TJ, McCance DR, Baynes JW. Accumulation of Maillard reaction products in skin collagen in diabetes and aging. Journal of Clinical Investigation, 1993 Jun. 91(6) :2463–9. 3-deoxyglucosone, an intermediate product of the Maillard reaction with an excitation wavelength of 370nm and an emission of 440 nm has also been characterized. Kato H, Hayase F, Shin DB, Oimomi M, Baba S. 3-Deoxyglucosone, an intermediate product of the Maillard Reaction. In Baynes JW and Monnier VM (1989)The Maillard Reaction in Aging, Diabetes, and Nutrition. Alan R. Liss, New York, pp69–84. Albumin has also been shown to form fluorescent products following glucose incubation with an excitation maxima at 278 nm and emission at 340 nm. Suarez G. Nonenzymatic browning of proteins and the sorbitol pathway. In Baynes JW and Monnier VM (1989) The Maillard Reaction in Aging, Diabetes, and Nutrition. Alan R. Liss, New York, pp141–162. Non tryptophan fluorescence development with excitation and emission maxima at 330nm and 405 nm respectively have been shown to occur with both glucose and fructose (Walton DJ, McPherson JD, Shilton BH. Fructose mediated crosslinking of proteins. In Baynes JW and Monnier VM (1989) The Maillard Reaction in Aging, Diabetes, and Nutrition. Alan R. Liss, New York, pp163–170.) and these fluorescent species have been shown to bind rather tightly to albumin and IgG thus being present in blood. Suarez G. Nonenzymatic browning of proteins and the sorbitol pathway. In Baynes JW and Monnier VM (1989) The Maillard Reaction in Aging, Diabetes, and Nutrition. Alan R. Liss, New York, pp141–162.

Diabetic patients were found to have significantly elevated levels of serum peptide and hemoglobin advanced glycosylation end products determined by radioreceptor assay and a competitive ELISA format. Makita Z, Radoff S, Rayfield EJ, Yang Z, Skolnik E, Delaney V, Friedman EA, Cerami A, Vlassara H. Advances glycosylation end products in patients with diabetic nephropathy. (1991) N Eng J of Med 325: 836-842. Makita Z, Vlassara H, Rayfield E, Cartwright K, Fridman E, Rodby R, Cerami A, Bucala R. Hemoglobin-AGE: A circulating marker of advanced glycosylation. (1992). Science 258:651–653. This latter method has also been used to show increased levels of advanced glycosylation end products on hemoglobin from diabetic humans compared to nondiabetic subjects and the values correlated with glycated hemoglobin values as quantified by HbAlc determination by high performance cation exchange liquid chromatography. Makita Z, Radoff S, Rayfield EJ, Yang Z, Skolnik E, Delaney V, Friedman EA, Cerami A, Vlassara H. Advances glycosylation end products in patients with diabetic nephropathy. (1991) N Eng J of Med 325:836–842. Streptozotocin treated diabetic rats have been shown to have ELISA detected increases in advanced glycosylation end products in the urine when compared to controls. Koenig RJ, Peterson CM, Kilo C, Cerami A, Williamson JR: Hemoglobin $A_{1c}$ as an indicator of the degree of glucose intolerance in diabetes. *Diabetes* 1976; 25:230–232. As noted, several investigators have found that advanced Maillard reaction products accumulate in skin collagen. McCance DR, Dyer DB, Dunn JA, Bailie KE, Thorpe SR, Baynes JW, Lyons TJ. Maillard reaction products and their relation to complications in insulin-dependent diabetes mellitus. J. Clin. Invest. 91: 2470–2478, 1993. Monnier VM. Toward a Maillard Reaction theory of aging. In Baynes JW and Monnier VM (1989) The Maillard Reaction in Aging, Diabetes, and Nutrition. Alan R. Liss, New York, pp1–21. Dyer DG, Dunn JA, Thorpe SR, Bailie KE, Lyons TJ, McCance DR, Baynes JW. Accumulation of Maillard reaction products in skin collagen in diabetes and aging, Journal of Clinical Investigation, 1993 Jun, 91 (6): 2463–9. All of the above methodologies require sampling of a biologics tissue or fluid; however, they do confirm the presence of late Maillard reaction products in plasma, red cells, and tissues.

SUMMARY OF THE INVENTION

It is an object of the present invention to provide a new and novel technique for the non-invasive measurements of advanced or late Maillard reaction products as well as other fluorescent chemical molecular species in blood and tissue. The present invention recognizes the fundamental problem of requiring a tissue biopsy or blood specimen to measure these compounds.

Instead of using the technique of chemical analysis of tissue or blood, the present invention takes advantage of the fluorescent molecular structure(s) of late or advanced Maillard products or melanoidins that occur in vivo. These molecules as noted above are stable to excitation with specific wavelengths and in return are capable of emission at specific wavelengths.

The present invention uses a suitable optical source to stimulate the molecules of interest into their excited state and then synchronously detects the subsequent characteristic emission by the molecules on their way back to their ground states. Specifically the present invention seeks out, upon a suitable stimulated excitation of blood and/or tissue, a particular wavelength of the relaxation emission that is characteristic and unique and spectrally distinct from the relaxation emissions of other molecular species that are also found in tissue (eg tryptophan) or blood (eg heme or hemoglobin with absorption between 400 and 600 nm). These latter spectra can be used as a denominator for tissue or blood advanced Maillard products to quantify the aging process in tissues, or glucose control over a period of approximately 120 days analogous to the use of glycated hemoglobin as the test is currently used clinically. In certain respects the present technique resembles that disclosed in U.S. Pat. No. 4,968,887 where gaseous nitrogen is detected using excited-state laser spectroscopy.

The present invention proposes to separate the readings in tissue from those in blood through the use of readings obtained with and without digital, ear or tissue compression to eliminate capillary blood from the excitation path. Thus the readings will be taken when the target for analysis is deplete and replete with blood allowing for both measurements of tissue and blood late Maillard products.

Major fluorophores with excitation-emission maxima at 328/378, 335/385, 360/460, 370/440, 278/340, and 330 nm/405 nm respectively will be quantified. Thus excitation will take place in the range of 270–370 nm and emission detected in the range of 370–460. The wavelength range for the excitation/emission radiation is fortuitous in that such radiation can pass without significant attenuation through the epidermis of the skin. The prototype site will include inter alia the backside of the index finger (opposite to the nail side) into the capillary bed to excite the molecules of interest in blood vessels and/or tissue following tissue compression to eliminate blood flow.

In order that the stimulated relaxation emission from the molecules of interest can exit from the epidermis of the backside of the index finger with minimal interference, the stimulating radiation is carefully focussed just inside the dermal layer and on the top part of the capillary bed that is closest to the epidermis. Thus the stimulated relaxation emission radiation from the excited molecules in tissue and/or blood has only to traverse a very short distance before being detected by a sensitive and calibrated detector assembly. The configuration will allow the detection of tissue fluorescence during compression to eliminate capillary blood and the sum of tissue and blood fluorescence. Thus blood fluorescence can be determined using the formula: blood value blood plus tissue reading (decompressed)— tissue reading (compressed). Further refinements include the normalization of readings to the characteristic spectra of tryptophan for tissue and hemoglobin for blood. In addition, doppler quantification of blood flow may be used to provide and independent and pulsatile assessment of blood content in the field of interest.

The present disclosed invention differs from the popular florescence spectroscopy method used for example by Bromberg in U.S. Pat No 4,055,768 in the design of an apparatus for measuring the concentration of fluorescent material in a specimen. The first one is the specificity of the spectral domain for the detection of advanced Maillard products. Second, the fluorescence spectra take the form of emission bands rather than well-defined spectral peaks as in the presently disclosed case. Since the visible absorption spectrum of the substance or substances involved is in general very complicated, it is difficult, if not impossible, to single out a spectral region of the florescence spectrum for detection that is characteristic of the substance in question without mixing up with others the substance's specific identity. Third, the method of fluorescence spectroscopy works best when the quenching of a characteristic fluorescence from a matrix is linked to the presence or absence of a particular substance to be identified or quantitatively determined as noted above with the use of compression to change the nature of the matrix. In this respect the currently disclosed technique of stimulated emission bears no resemblance whatsoever.

The novel features that are believed to be characteristic of the invention both as to organization and method of operation, together with further objects and advantages thereof, will be better understood from the following description considered in connection with the accompanying drawings in which preferred embodiments of the invention are illustrated by way of examples. It is to be expressly understood; however, that the drawings are for the purpose of illustration and description only and are not intended as a definition of the limits of the invention.

DESCRIPTION OF THE PREFERRED EMBODIMENT

Figure 1:
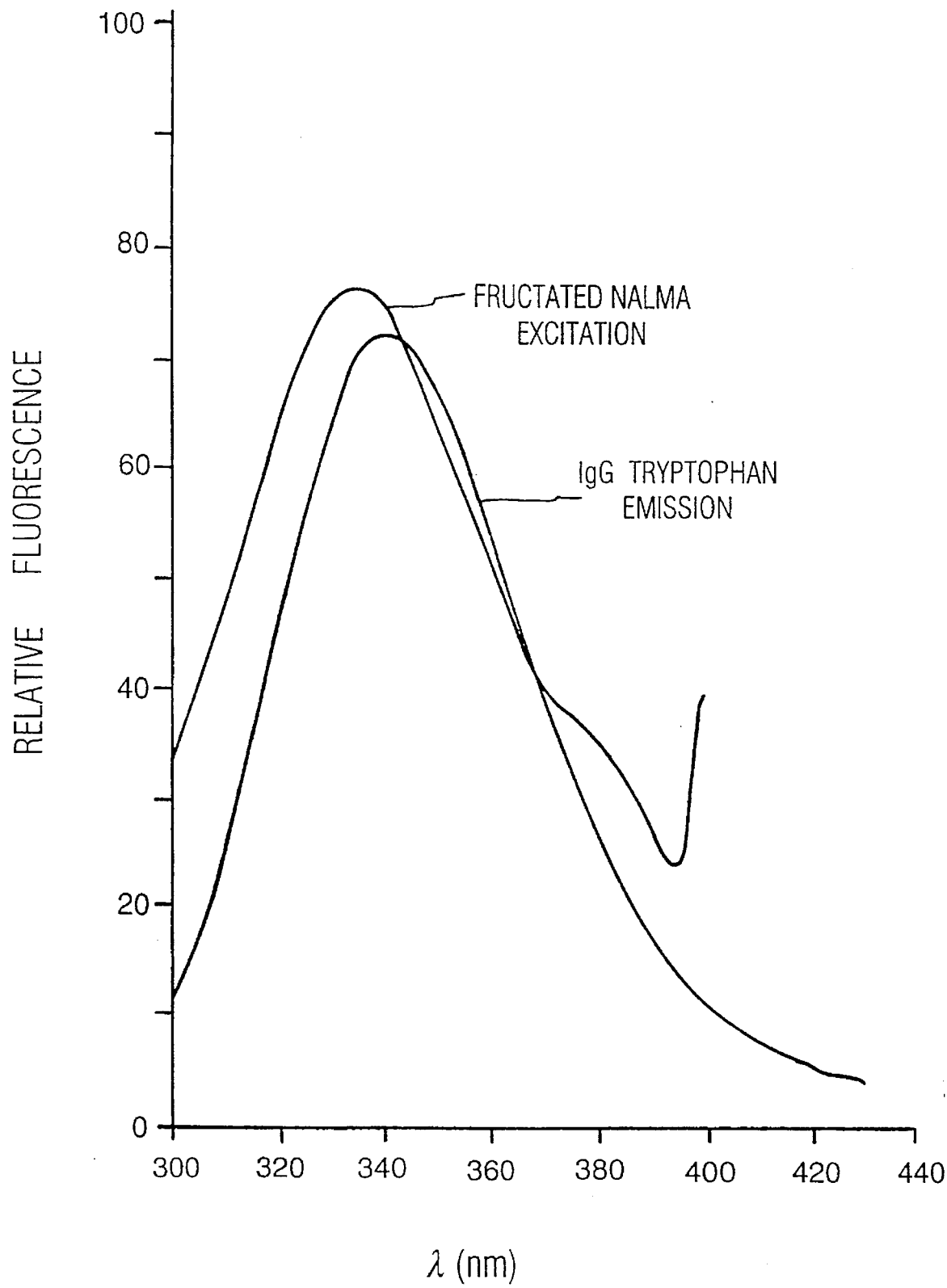
FIG. 1 a characteristic excitation/fluorescence spectra for a typical Maillard product bound to albumin.
Figure 2:
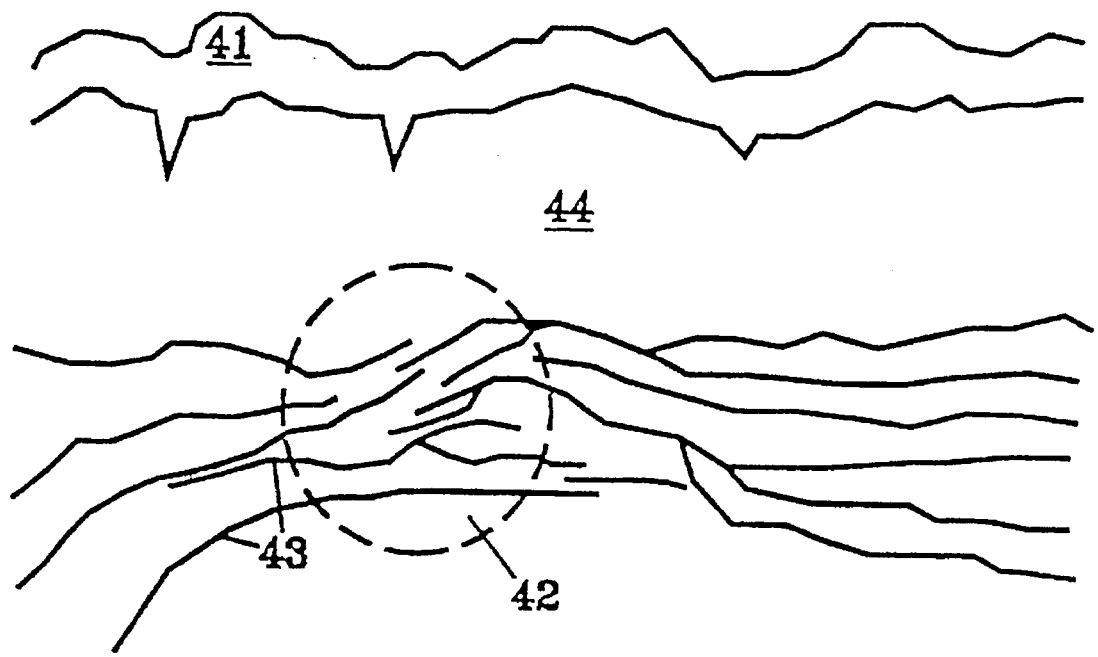
FIG. 2 is a pictorial illustration of the epidermis of the skin of the finger showing sections of the dermis, capillary bed, and blood vessels. The distance between the blood vessels and the top surface of the epidermis is typically 0.3 mm.

The invention will be illustrated for the case of a noninvasive, blood late Maillard products concentration detector, but, as indicated above, this invention is also applicable to testing solute concentrations in many different types of solutions and in other environments, such as a sample contained within a test tube or smeared onto a slide. In this process of measuring the concentration of a component of a blood sample, light of wavelength in the range from 270–370 nm is directed at a portion of a person or animal's epidermis to pass into a blood-rich region of that person or animal to excite the blood late Maillard products in the user's blood. As is illustrated in FIG. 2, this radiation is focussed, through the epidermis 41 of the front side of the index finger (i.e., the side that is opposite to the nail side of the finger) and a derm layer 44, to a point on the top part of the capillary bed 42 that is closest to the epidermis onto the capillary bed to excite the Maillard products in blood vessels (see FIG. 1). This region is selected for exposure because it is a blood-rich region, having many blood vessels 43, closely spaced (about 0.3 mm) from the epidermis. Although any finger can be used, it is preferred that the least calloused finger be used to achieve improved penetration of the excitation radiation into that finger.

Figure 3:
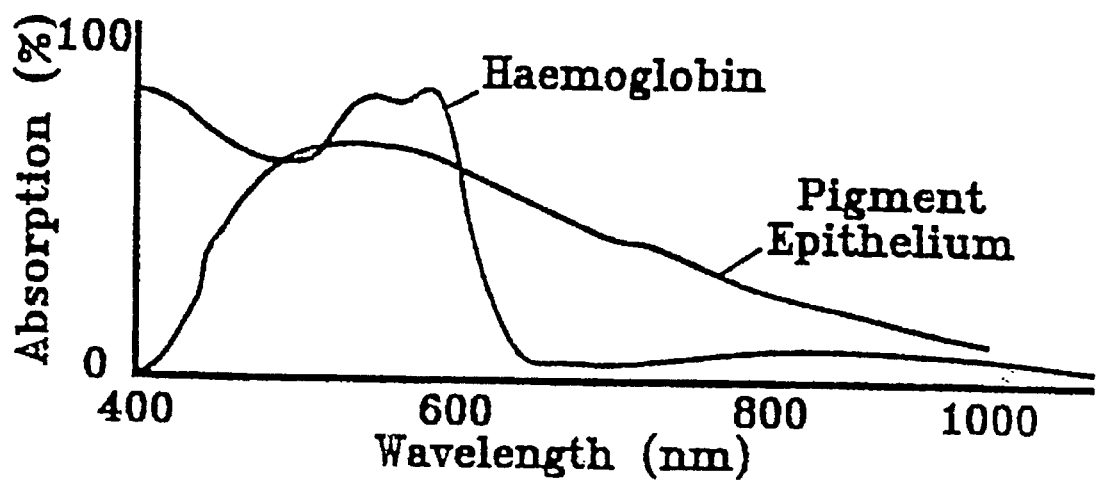
FIG. 3 is a transmission versus wavelength plot showing the absorption characteristic of hemoglobin and pigment epithelium as a function of spectral wavelength.

The 270–370 nm range is selected for the exposing light because it can pass, without significant attenuation, through the epidermis 41 (see FIG. 2). Preferably, the exposing light is within the range from 200–600 nm because this range not only passes through the epidermis without undue attenuation, as illustrated in FIG. 3, it is also effective in exciting hemoglobin molecules, so that pressure-related changes in the amount of blood in capillary bed 42 can be compensated for from a knowledge of the amount of absorption by the hemoglobin molecules.

This exposing light not only excites blood Maillard products and hemoglobin molecules into an excited state, it also stimulates emission of light from such excited molecules. Because the incident light need only travel through about 0.3 mm of tissue, the exposing beam will not be significantly attenuated prior to exposing the blood in the capillary bed. Because the emitted light likewise need travel only through about 0.3 mm of tissue before incidence on a detector, it will likewise not be significantly attenuated. Because of this, the detected signal will be much larger than in prior techniques. The detected intensity of light is utilized to calculate the concentration of blood late Maillard products.

Several optical sources, such as semiconductor LEDs and semiconductor laser diodes, can produce light at 200–600 nm. Because the probability of a Maillard product's excitation in a beam of intensity on the order of 5 Watts/cm$^2$ is expected to be very small (typically around 10$^{-4}$ or smaller), it is important that the source of the exposing light emit adequate optical power in the right wavelength, in order to be effective as an excitation source. Because this exposing light plays the dual role of exciting blood late Maillard products molecules into excited states and stimulating emission from such excited molecules, the rate of emission is proportional to the square of the intensity of this light. Therefore, the rate of emission is proportional to the square of the power of the excitation radiation. Therefore, it is advantageous to focus this light onto a small area of the capillary bed 42. Preferably, this area has a diameter on the order of a few tens of microns, but diameters of up to 100 microns are also adequate. The depth of focus should also be on the order of the thickness, 100 microns, of the capillary bed. Semiconductor LEDs and semiconductor laser diodes typically have output powers in excess of 100 mW and higher and with proper delivery optics these output power levels are more than adequate for the currently disclosed blood late Maillard products measurement technique. Superradiant diodes are advantageous because of their particularly large beam intensity. An ultraviolet flashlamp could also be utilized as the light source.

It is advantageous for the optical source to be substantially monochromatic, because monochromatic or substantially monochromatic light can be focussed onto a very tiny region with inexpensive optical components that do not correct for chromatic aberration. Such accurate focussing is needed to be able to focus this light accurately onto the top part of the capillary bed that is closest to the epidermis and to obtain the desired spot size. In addition, because the rate of emission is proportional to the square of the intensity of this light, such concentrated focussing of the light will greatly increase the rate of stimulated emission. Light emitting diodes (LEDs), emitting in the super-radiant mode, and semiconductor laser diodes meet all of these criteria for the optical source. Diode lasers of wavelength 0.67 microns are readily available with a bandwidth of 0.1 A, FWHM. At a modest increase in cost, laser diodes having a bandwidth of 0.01A are also available. An additional advantage of such sources is that they are relatively inexpensive so that low cost, non-invasive blood late Maillard products monitors can be produced.

Figure 4A:
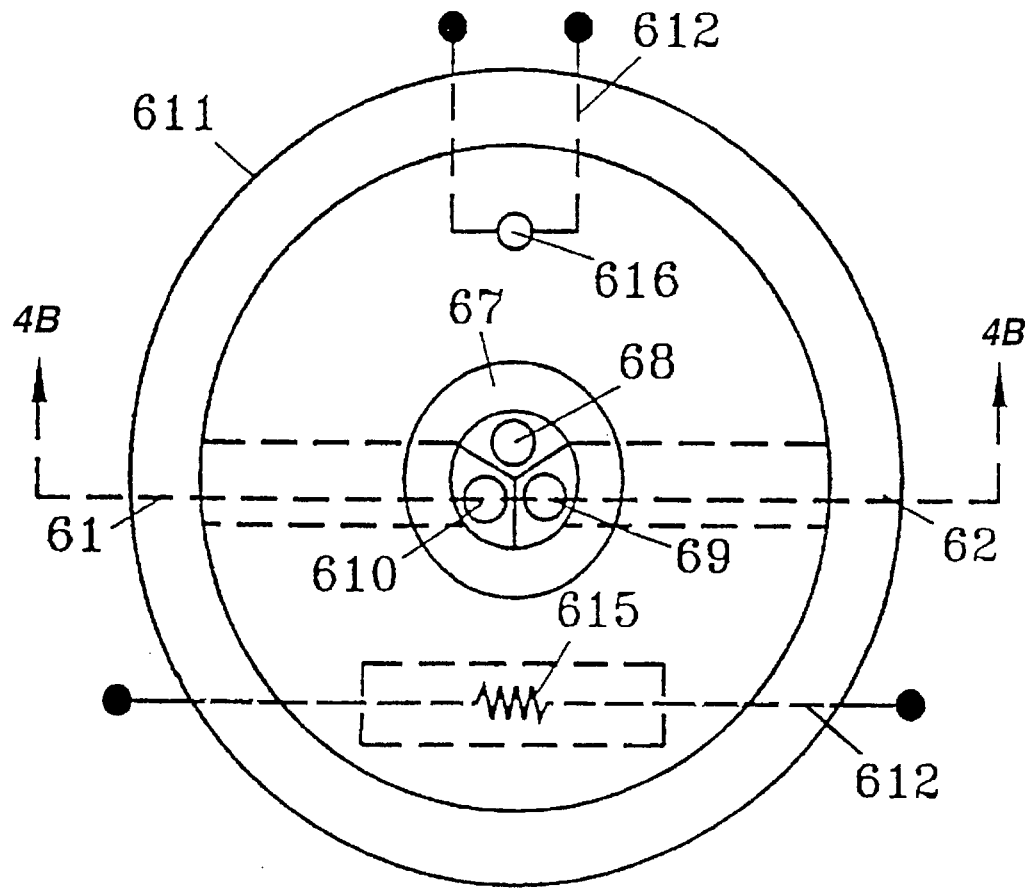
FIG. 4A and 4B are top plan and side cross-sectional views, respectively, of a first embodiment of a non-invasive low-cost, blood late Maillard products concentration detector.
Figure 4B:
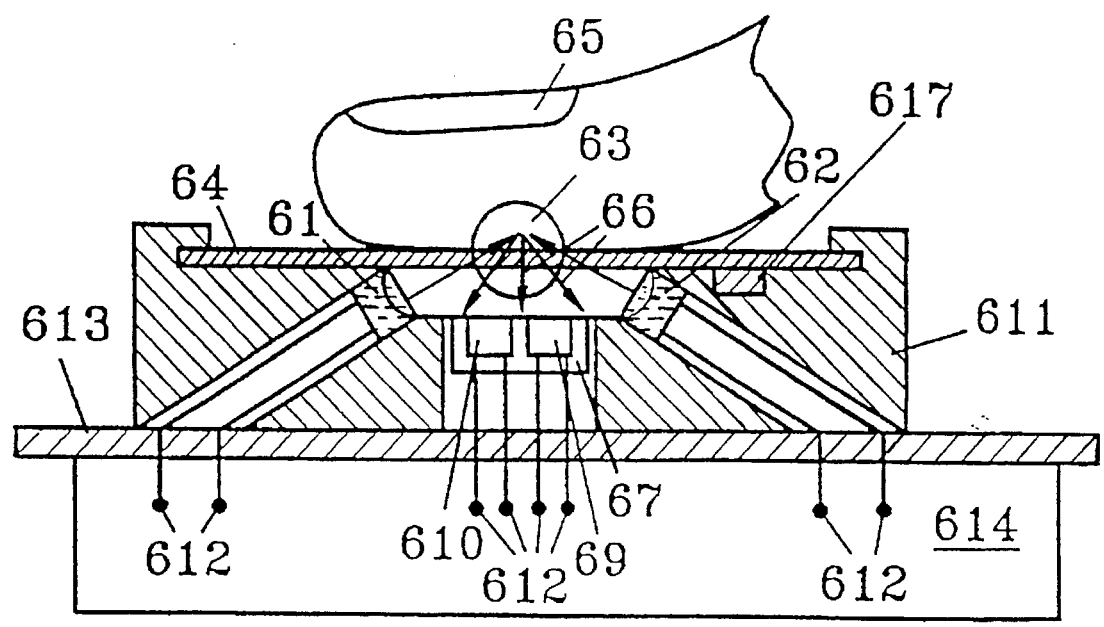

FIGS. 4A and 4B are top plan view and side cross-sectional views, respectively, of a first embodiment of a non-invasive, low-cost, blood late Maillard products concentration detector. A pair of excitation light sources 61 and 62, such as LEDs or laser diodes, focus excitation radiation of wavenumber 1040 cm$^{-1}$ into a spatially small focal region 63 approximately 0.3 mm beyond an optically flat plate 64 that is transparent to both the excitation radiation and the subsequent relaxation emission radiation. Many choices of material, such as ZnS and ZnSe, are possible for this flat plate. This plate is "transparent" to light of a given wavelength if its absorptivity is less than a few percent for such light.

During a blood late Maillard products concentration test, a user presses a front side (i.e., the side opposite to that person's nail) of his or her finger 65 against this plate, so that the excitation radiation beam can be accurately focussed onto the top of the capillary bed 42. This point of focus is chosen because the numerous small blood vessels 43 within the capillary bed provide one of the closest locations of blood to a patient's epidermis and because a finger is conveniently pressed against plate 64 during testing. The Maillard products and hemoglobin molecules are excited by the excitation radiation and, upon returning to their ground states, emit radiation 66 that is characteristic of the Maillard product molecules. Although other wavelengths of relaxation radiation are also emitted by the Maillard product molecules, they are not uniquely emitted by Maillard product molecules and therefore are not as easily utilized to measure the concentration of Maillard product molecules.

Detector assembly 67 includes three infrared detectors 68, 69 and 610, each of which occupies about one-third of the total field of view subtended by the detector assembly 67 at the small focal region 63 of excitation radiation. Detectors 68, 69 and 610 are each housed in a separate compartment to prevent cross-talk or light leakage between them. Detectors 68, 69 and 610 each includes its own unique narrow band-pass interference filter passing only radiation at 378 nm, 9.02 microns and 3.80 microns respectively. As will be explained in greater detail below, these choices of filters enable a measured concentration of Maillard product molecules to be produced that is unaffected by the temperature and touching pressure of the patient's finger.

The excitation light sources 61 and 62 and the detector assembly 67 are mounted inside a circular sensor housing 611 in such a way that a set of electrical leads 612 from the sources and detector assembly all come out from one side of detector assembly 67 opposite to that of the optical flat plate 64. Leads 612 can be conveniently soldered to a printed circuit board (PCB) 613 that contains processing electronic circuits 614 and also supports the overall sensor housing 611. The sensor housing 611 is temperature regulated at a temperature $T_o$ of approximately 37° C. (i.e., normal human body temperature) by means of a heater resistor 615 and a thermistor 616 imbedded therein. The electrical leads 612 of heater resistor 615 and thermistor 616 are also routed to the PCB 613 that also contains a temperature regulating circuit.

The narrow band-pass, interference filter included within detector 610 passes a narrow range of light centered at wavenumber 2,632 cm$^{-1}$ (wavelength 3.8 microns). This light is primarily blackbody radiation from the optical flat plate 64 and from those portions of detector assembly 67 immediate adjacent to this plate. The output of this detector provides information about any temperature changes caused by internal or external environmental changes, such as by the fore finger of the patient touching the optical flat plate during the blood late Maillard products measurement itself. The relationship between the instantaneously measured signal from detector 610 and the instantaneous temperature T(t) measured in degree Celsius is given by $$I_s(t)=I_0\times[(T(t)+273)/T_0+273)]^4$$

where $I_s(t)$ is the instantaneous output signal of detector 610, $I_o$ is the output at $T_0°$ C. and $T(t)°$ C. is the instantaneous spatially averaged temperature of the cavity surrounding the detector assembly 67.

The narrow band-pass, interference filter included within detector 69 passes a narrow range of light centered at 9.02 microns. Detector 69 receives radiation from three separate sources: (i) blackbody radiation from the cavity surrounding detector assembly 67 (which includes optical flat plate 64); (ii) relaxation radiation from hemoglobin inside the blood vessels; and (iii) relaxation radiation from the Maillard product molecules inside the blood vessels. As discussed in greater detail below, the output signal of detector 69 is needed to eliminate the effect of the variable touching pressure of the fore finger on the optical flat plate 64 during measurement, because the volume of blood and the quantity of hemoglobin in the blood vessels within the region exposed by the exposing light, is dependent of how hard the finger is pressed against optical flat plate 64. This blood volume is a function of this pressure because the touching pressure forces blood out of the capillary bed 42 in the region of the fore finger that is in contact with optical flat plate 64.

The narrow band-pass, interference filter included within detector 68 passes a narrow range of light centered at 378 nm. Detector 68 receives radiation from two different sources: (i) relaxation radiation from the Maillard product molecules in the blood vessels; and (ii) blackbody radiation from the cavity surrounding detector assembly 67. The output signal of detector 68 therefore contains information relating to the amount of blood late Maillard products in the blood vessels of the patient under test.

By processing the three signals received respectively from detectors 68, 69 and 610, a net output signal is produced that indicates the concentration of Maillard product molecules in the blood and is not affected by the temperature and touching pressure of the patient's finger on the optical flat plate. This processing is well known from basic algebra. Let $I_s(t)$, $J_s(t)$ and $K_s(t)$ be the outputs, as a function of time t, of detectors 610, 69 and 68, respectively during a particular blood late Maillard products measurement routine. $I_s(t)$ is a function of the instantaneous temperature T(t) of the cavity surrounding the detector assembly 67 including the optical flatplate 64. $J_s(t)$ is the sum of blackbody radiation at temperature T(t) and the relaxation radiation from hemoglobin and the Maillard product molecules in the blood vessels when these vessels are exposed by light from excitation light sources 61 and 62. $K_s(t)$ is the sum of the blackbody radiation at temperature T(t) and the relaxation radiation from the Maillard product molecules when the latter is stimulated by the excitation light sources 61 and 62.

When no patient's finger is in contact with optical flat plate 64, the temperature of the cavity immediately surrounding the detector assembly 67 (including the optical flat plate) is regulated by thermistor 612 and heater resistor 615 to a temperature $T_0$ of 37° C. This temperature is selected because it should most closely match the actual temperature of a patient's finger. The outputs from detectors 610, 69 and 68 under this condition are represented as $I_0$, $J_0$ and $K_0$, respectively, and they represent only the blackbody radiation received at the wavelengths defined by the narrow band-pass filters of each of the respective detectors.

When the patient's finger touches the optical flat plate 64, the cavity and plate temperatures change to a slightly different temperature T(t) and the outputs from the detectors 68, 69 and 610 are, respectively:

$$I_s(t) = I_0 \times [T(t)/T_0]^4 \quad \text{(Ia)}$$

$$I_s(t) = I_0 \times [T(t)/T_0]^4 + G[H(t)] + H(t) \quad \text{(Ib)}$$

$$K_s(t) = K_0 \times [T(t)/T_0]^4 + G[H(t)] \quad \text{(IC)}$$

where H(T) is the component of the output currents produced by relaxation radiation from hemoglobin molecules and G[H(T)] is the component of the output currents produced by relaxation radiation from Maillard product molecules. $I_0$, $J_0$ and $K_0$ are known constants determined from measurements made when no patients finger is present in the test apparatus. Measurement of the three parameters $I_s(t)$, $J_s(t)$ and $K_s(t)$ enables the three unknowns H(t), G[H(t)] and T(t) to be determined by standard methods from basic algebra.

The amount of relaxation radiation from Maillard product molecules depends on the number of Maillard product molecules, which in turn is proportional to the blood volume being excited. The function H(t) measures the relaxation radiation coming only from the hemoglobin molecules and is therefore a function of the blood volume being excited, which is why G is written as a function of H(t). To first order in the pressure P(t)

$$H(t) = \Omega P(t)$$

where $\Omega$ is a constant determined during a calibration procedure and where P(t) is measured separately by a pressure sensor 617 before and during the blood late Maillard products measurement.

In actual use of the non-invasive blood late Maillard products concentration detector, the patient is guided to press his or her finger onto flat plate 64 with a pressure that is within a preselected pressure range. When the patient's finger applies pressure within this range, a green light is illuminated to indicate that this pressure is within the desired range. This range is selected to ensure that the volume of illuminated blood is within a range such that H(t) can be accurately represented by equation (1) above.

Figure 5:
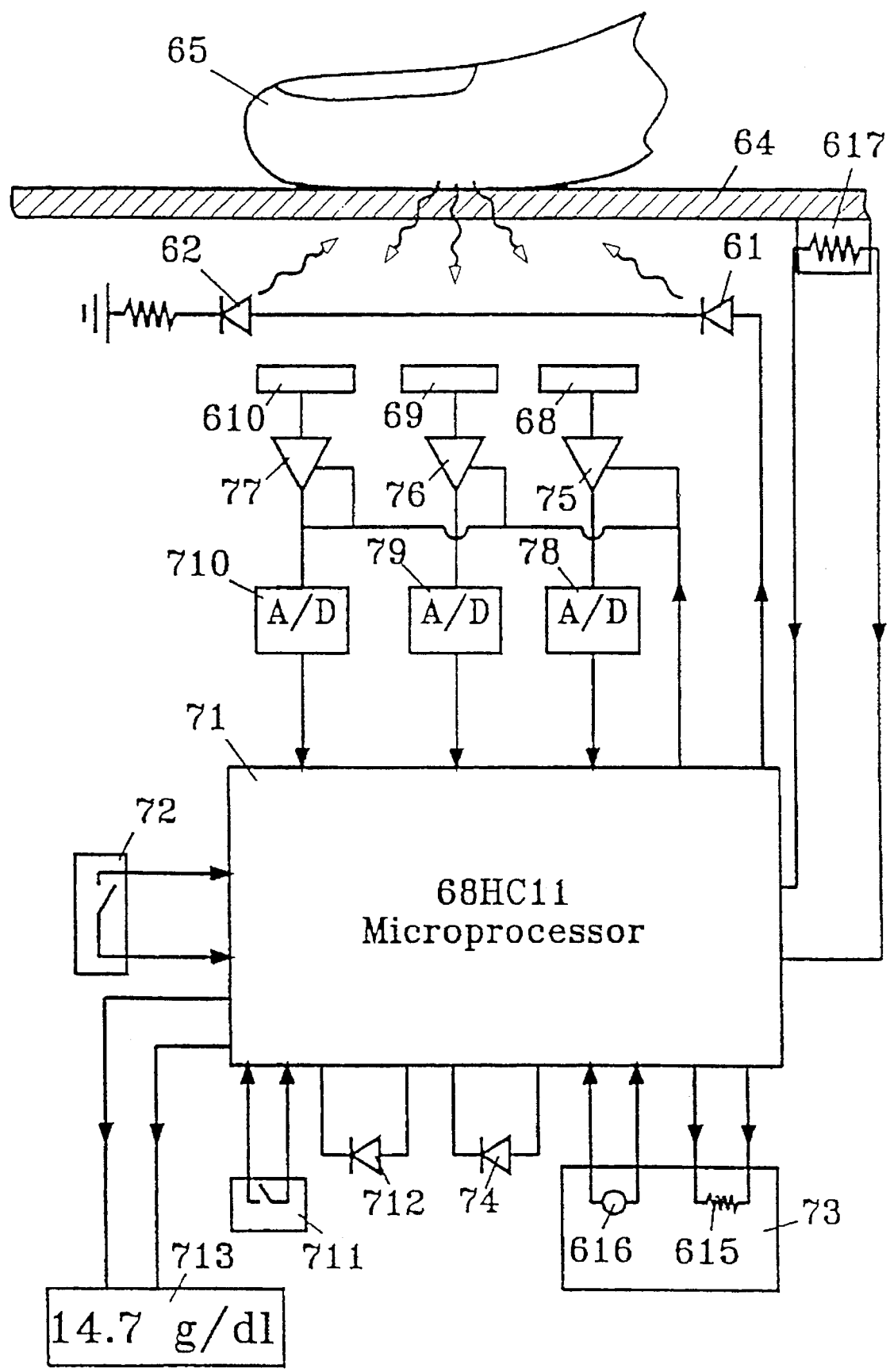
FIG. 5 is an electronic block diagram of the signal processing components of the preferred embodiment.

The signal processing electronics of this blood late Maillard products concentration detector is illustrated schematically in FIG. 5. A low-cost, low-power processor 71, such as the model 68HC11 single-chip, 16-bit microprocessor manufactured by Motorola, is used to control operation and to perform all calculations. When microprocessor 71 receives an ON signal from a manual ON/OFF switch 72, it activates temperature regulation circuitry 73 which controls the temperature of sensor housing 611 by means of heater resistor 615 and thermistor 612. When the temperature of sensor housing 611 reaches the preselected temperature $T_0$ (approximately 37° C.), a temperature ready light 74 is turned on and microprocessor starts pulsing excitation light sources 61 and 62 at a frequency of F hertz (e.g., 60 Hz). Signals from detectors $I_s(t)$, $J_s(t)$ and $K_s(t)$ from detectors 68, 69 and 610, respectively, are amplified by preamplifiers 75–77 and A/D converters 78, 79 and 710, respectively. Because no finger is pressed against flat plate 64 at this point in the measurement process, the radiation detected by detector assembly 67 (which contains detectors 68, 69 and 610) is just blackbody radiation emanating from the sensor housing cavity, including the optical flat plate 64.

When microprocessor 71 receives an initialization signal from a manual switch 711, the outputs of A/D converters 78, 79 and 710 are stored and represent the values of $I_0$, $J_0$ and $K_0$, respectively. After the initialization routine has completed, a measurement ready light 712 begins to blink, indicating that the blood late Maillard products concentration detector is ready. The patient is then to press his or her finger against flat plate 64. When pressure sensor 617 detects a pressure against flat plate 64 in the preselected pressure range, measurement ready light 712 converts from a blinking mode to a steady mode, thereby indicating that the actual blood late Maillard products measurement has commenced. When the patient sees the measurement ready light 712 is steady, he or she should try to apply a constant pressure until light 712 begins blinking again. Changes in pressure should affect concentration measurements of Maillard product and hemoglobin substantially by the same multiplicative factor so that the ratio of Maillard product and hemoglobin concentrations is not significantly affected by changes in pressure during the measurement. Concurrently, a liquid crystal display (LCD) 713 displays the blood late Maillard products concentration.

During the interval in which ready light 712 is steady, microprocessor 71 acquires the values $I_s(t)$, $J_s(t)$ and $K_s(t)$ and solves the three equations (Ia), (Ib), and (Ic) above to produce the value of the blood late Maillard products concentration of the patient. At the end of this data acquisition and computation phase, measurement ready light 712 again begins to blink, thereby indicating that it is ready to perform another blood late Maillard products concentration measurement. If desired, the patient can initiate another measurement simply by removing his or her finger from the optical flat plate, waiting for a couple of minutes and then repeating the measurement procedure. If at any time during a measurement, the pressure on flat plate 64 is outside of the preselected range, ready light 712 turns off and the measurement is voided.

Calibration of this low-cost, non-invasive blood late Maillard products concentration detector is achieved by determining the value of $\Omega$ in equation (1) above. This can be done by a patient by measuring a sample of blood with the present blood late Maillard products concentration detector and by concurrently drawing a sample of blood in which the ratio of blood late Maillard products concentration to hemoglobin concentration is determined by another blood late Maillard products concentration detector that is known to be accurate. The ratio of these two values can be used by the patient to multiply the output of LCD 713 to produce an accurate concentration value. In some models, an input mechanism can be included that allows the user to input this ratio into microprocessor 71 so that this correction factor can be applied automatically by microprocessor 71. Alternatively, the user would have to take the value calculated by the instrument and scale it according to the results of the calibration measurement.

Figure 6A:
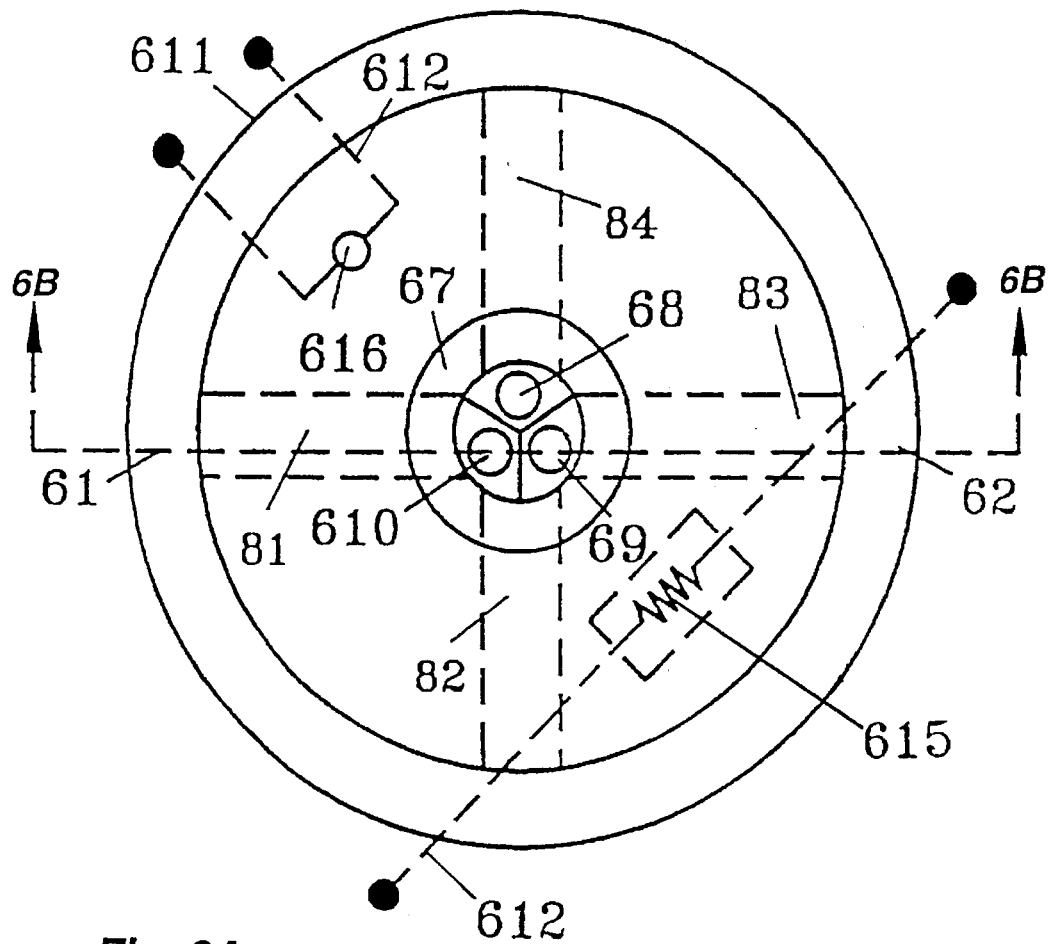
FIGS. 6A,and 6B illustrate an alternate embodiment of the non-invasive, low-cost blood late Maillard products concentration detector of FIGS. 4A and 4B, having four excitation light sources.
Figure 6B:
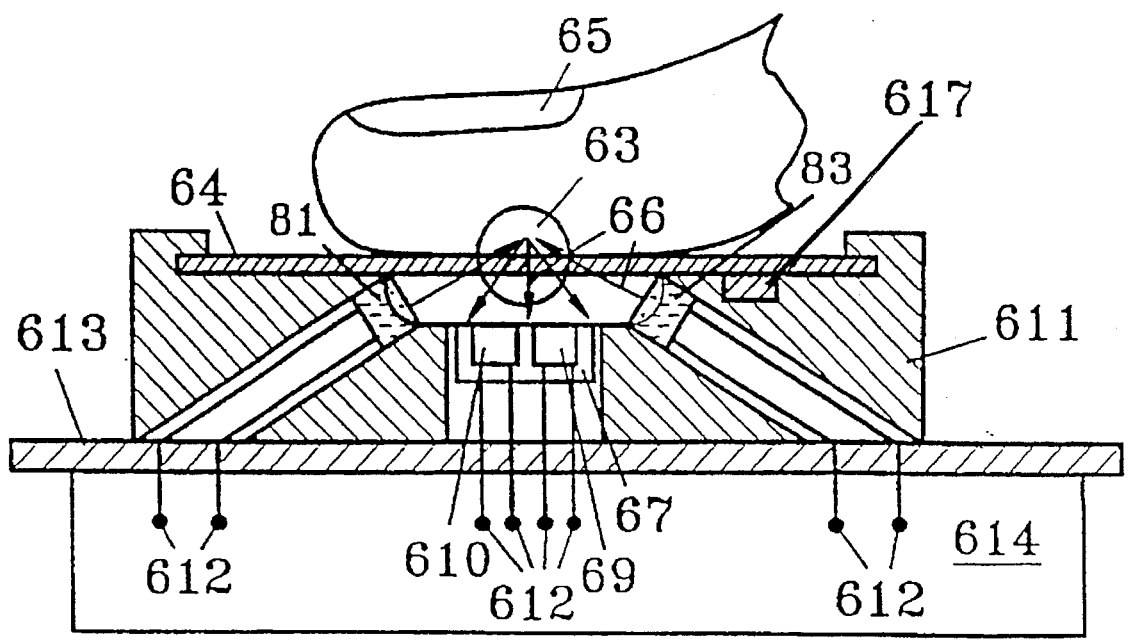

FIGS. 6A and 6B illustrate an alternate embodiment of sensor housing 611 that includes four excitation light sources 81–84 instead of two excitation light sources 61 and 62 as in the embodiment of FIGS. 4A and 4B. The use of four or more excitation light sources enhances the signal level of the relaxation radiation from both hemoglobin and Maillard product molecules, because of the resulting increase in excitation light energy density. This increases the signal-to-noise ratio of the emitted light received by detector assembly 67.

Figure 7A:
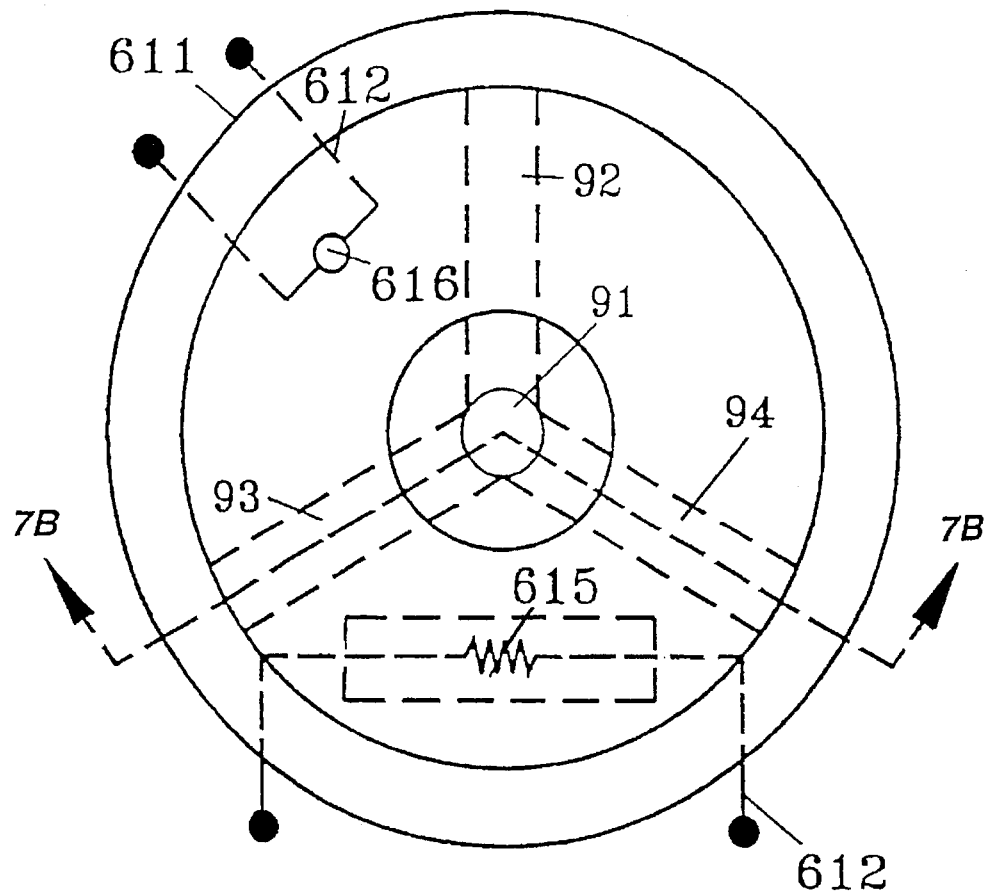
FIGS. 7A and 7B illustrate an alternate embodiment of the low-cost, non-invasive blood late Maillard products detector of FIGS. 4A and 4B, having three detectors spaced around a central source.
Figure 7B:
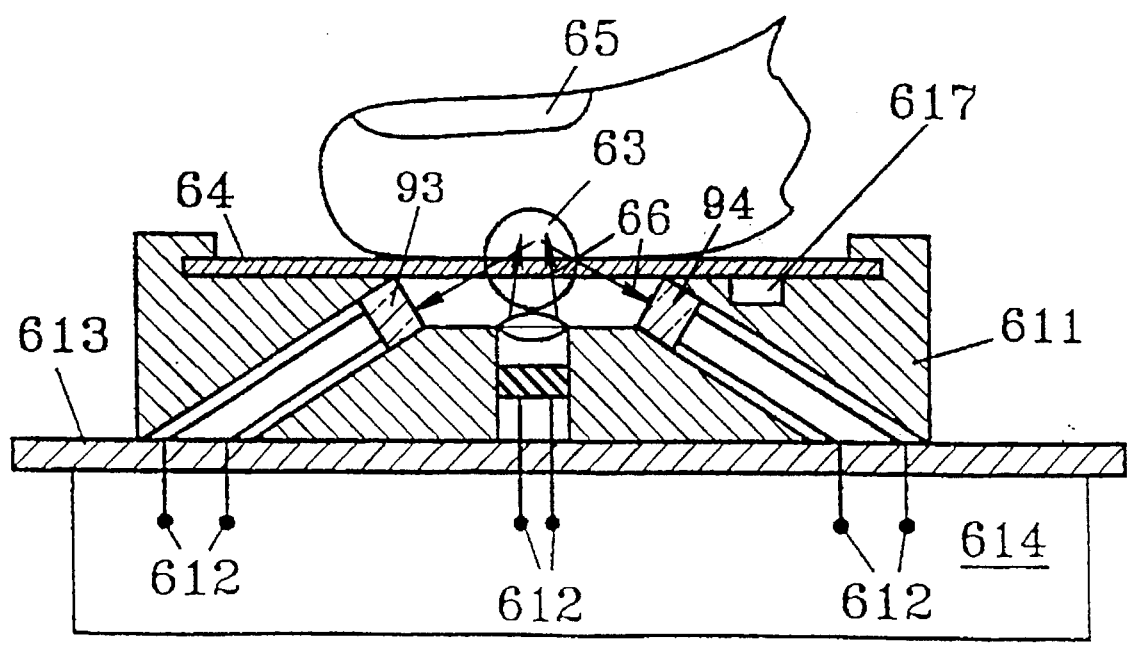

FIGS. 7A and 7B illustrate an alternate embodiment of the low-cost, non-invasive blood late Maillard products concentration detector of FIGS. 4A and 4B, having three detectors spaced around a central optical source. A single excitation light source 91 is centered laterally within sensor housing 611. Excitation radiation is focussed by a relatively long focal length, achromatic doublet or triplet lens system onto a small focal region 63 just beyond optical flat plate 64. Three detectors 92–94 are located symmetrically about a central axis of sensor housing 611 to collect stimulated relaxation radiation from a patient's finger 65. Detectors 92–94 are each equipped with a different narrow bandpass, interference filter that passes radiation only at 378 nm, 9.02 microns (1,109 cm$^{-1}$) and 3.80 microns (2,632 cm$^{-1}$), respectively.

Figure 8A:
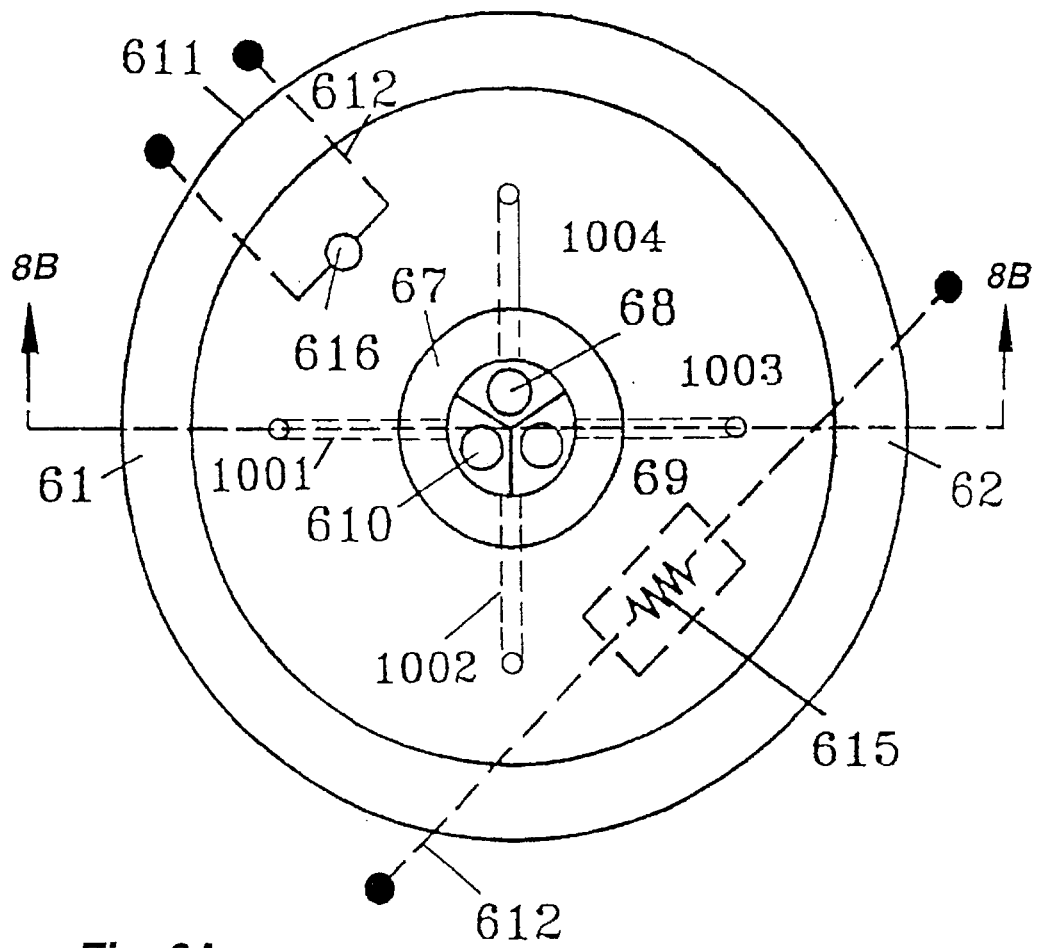
FIGS. 8A and 8B illustrate an alternate embodiment of the low-cost, non-invasive blood late Maillard products concentration detector of FIGS. 4A and 4B that uses optical fibers for light sources.
Figure 8B:
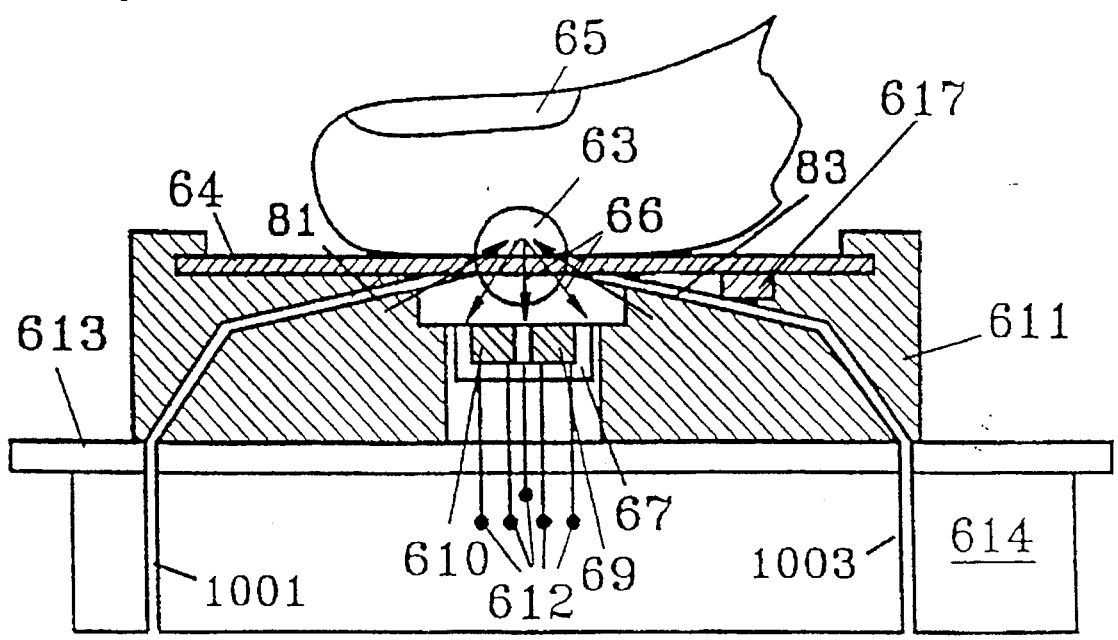

FIGS. 8A and 8B illustrate an alternate embodiment of the low-cost, non-invasive blood late Maillard products concentration detector of FIGS. 4A and 4B. In place of the two excitation light sources 61 and 62 of the embodiment in FIGS. 4A and 4B are at least two optical fibers 1001–1004 arranged symmetrically about a longitudinal axis of sensor housing 611. This particular embodiment utilizes four such optical fibers. Excitation light is piped through the optical fibers and focussed onto a small focal region 63 just beyond the optical flat plate 64 as before. The use of optical fibers as the carriers of the excitation radiation enables the detector assembly 67, containing detectors 68, 69 and 610, to be mounted very close to focal region 63, thereby significantly increasing the solid angle within which these detectors receive light from focal region 63. This provides a concomitant increase in the signal to noise ratio of this concentration detector.

Figure 9A:
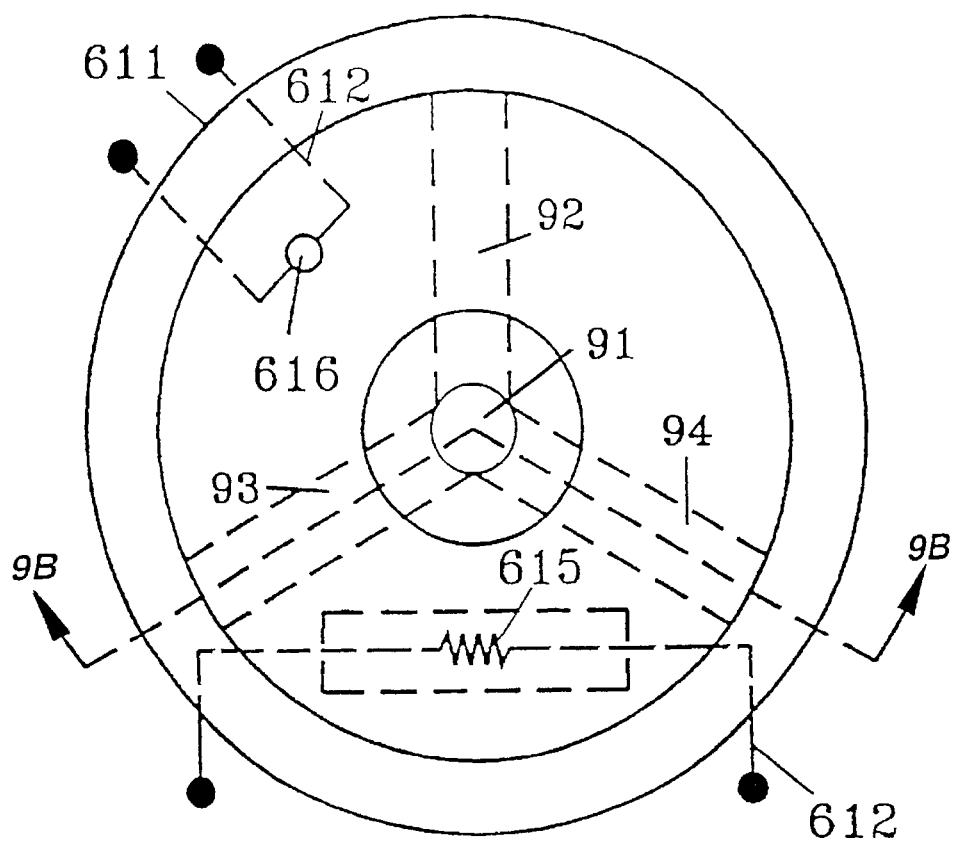
FIGS. 9A and 9B illustrate an alternate embodiment of the low-cost, non-invasive blood late Maillard products concentration detector of FIGS. 7A and 7B in which a single excitation light source is replaced by a single optical fiber.
Figure 9B:
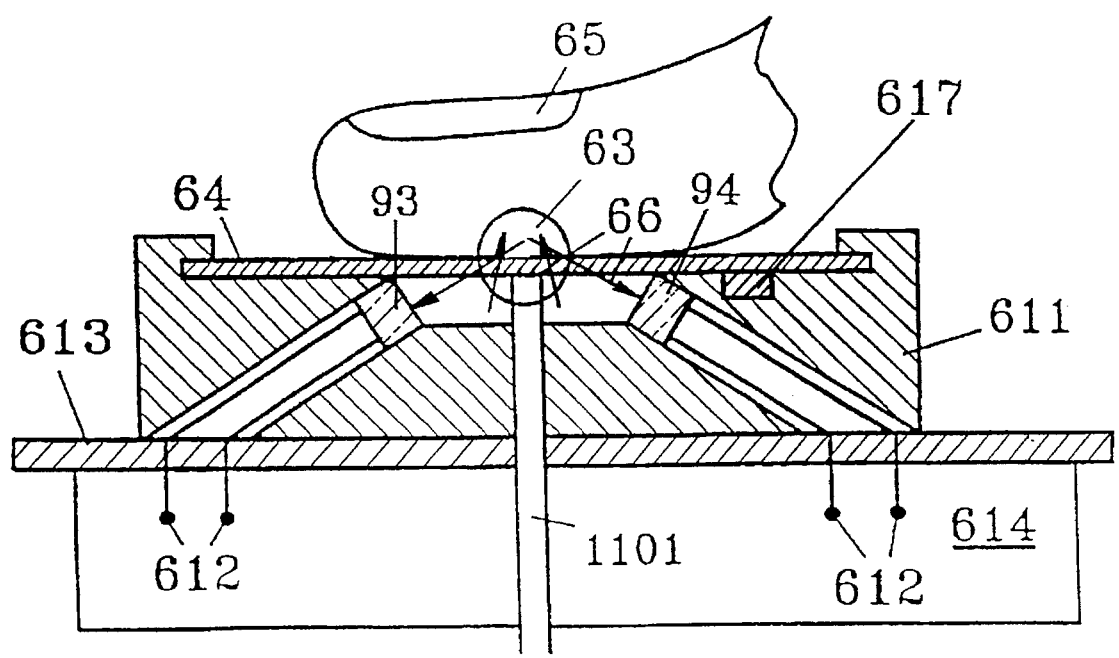

FIGS. 9A and 9B illustrate an alternate embodiment of the low-cost, non-invasive blood late Maillard products concentration detector. The only difference between this embodiment and the embodiment of FIGS. 7A and 7B is that single excitation light source 91 is replaced by a single optical fiber 1101 that transports light from a remote location.

Figure 10A:
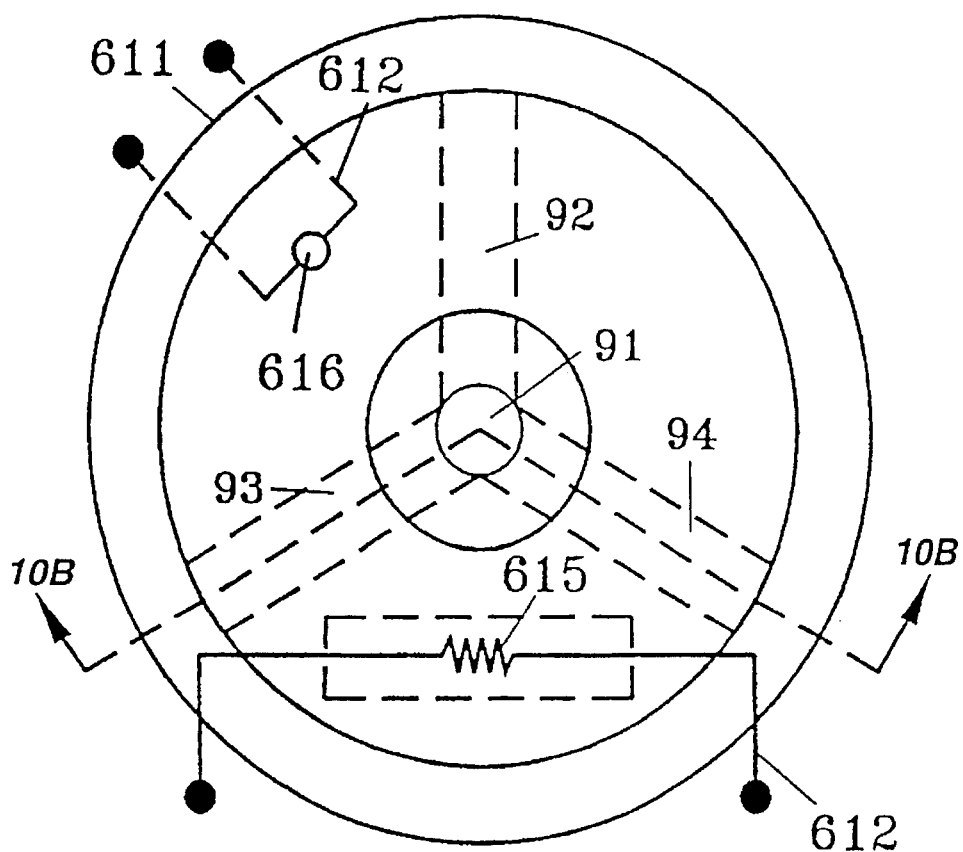
FIGS. 10A and 10B illustrate an alternate embodiment of the low-cost, non-invasive blood late Maillard products concentration detector of FIGS. 9A and 9B in which the optical fiber penetrates the flat optical plate.
Figure 10B:
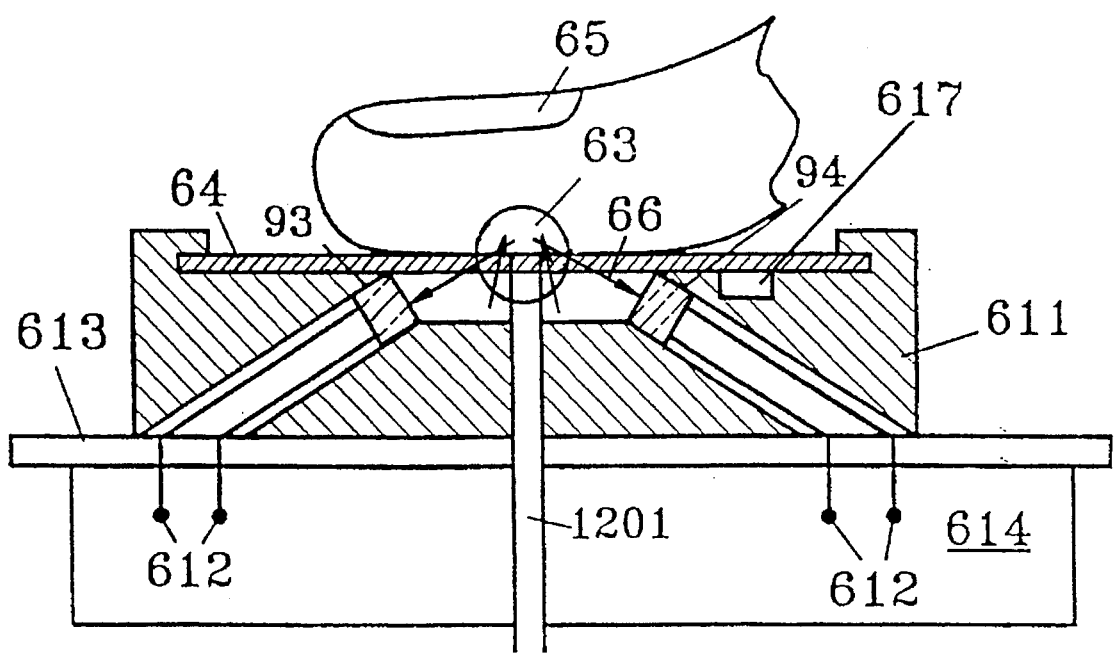

FIGS. 10A and 10B illustrate an alternate embodiment of the low-cost, non-invasive blood late Maillard products concentration detector. In contrast to the embodiment of FIGS. 9A and 9B, optical fiber 1201 penetrates through optical flat plate 64. Because the excitation light does not now pass through optical flat plate 64, this plate can be made out of a different and less expensive material, such as silicon. Silicon blocks all radiation of wavelength less than about one micron, but has good transmission characteristics in the medium to far infrared. The other embodiments require that flat plate 64 be made of a material, such as ZnS or ZnSe, that transmits radiation from the visible all the way to the medium and far infrared. In general, ZnS and ZnSe plates are significantly more expensive than silicon plates.

The foregoing detailed description is illustrative of the invention and it is to be understood that additional embodiments thereof will be obvious to those skilled in the art. This description, together with those additional embodiments obvious to those skilled in the art, are considered to be within the scope of the invention.

What is claimed is:

1. A non-invasive, blood chemistry measurement apparatus for measuring a concentration of a selected blood component within a sample of blood, said apparatus comprising:

a source of light in the wavelength range from 200–600 nm, whereby this light can pass through a person's epidermis without undue absorption by the epidermis;

means for detecting light that is emitted from molecules of the selected blood component in response to light from said source of light; and means, responsive to said means for detecting, for calculating a concentration of said selected blood component.

2. An apparatus as in claim 1 wherein said means for detecting comprises a detector that is responsive substantially only to light at a wavelength that is emitted substantially only by molecules of said selected blood component.

3. An apparatus as in claim 1 wherein said means for detecting produces N signals $S_1, \ldots, S_N$, where N is greater than 1, and wherein said means for calculating a concentration is responsive to these N signals to calculate the concentration of said selected blood component.

4. An apparatus as in claim 3 wherein said means for detecting detects only light in a set of N wavelength bands and wherein each $S_k$, for k=1, . . . , N, is proportional to an intensity of light in the kth of these wavelength bands.

5. An apparatus as in claim 4 wherein said means for detecting comprises a set of N detectors, each of which detects light only in a uniquely associated one of these N wavelength bands.

6. An apparatus as in claim 3 wherein N=2, wherein $S_1$ is proportional to an intensity of light within a band substantially centered on an emission peak of blood late Maillard products substantially at 378 nm, wherein $S_2$ is proportional to an intensity of light within a band substantially centered on an emission peak of hemoglobin substantially at wavenumber 1,109 cm$^{-1}$, and wherein a calculated concentration of blood late Maillard products is corrected by use of S2 to take into account effects due to changes in blood volume intersected by the light from said light source.

7. An apparatus as in claim 3 wherein N=3, wherein $S_1$ is proportional to an intensity of light within a band substantially centered on an emission peak of blood late Maillard products substantially at wavenumber 1,040 cm$^{-1}$, wherein $S_2$ is proportional to an intensity of light within a band substantially centered on an emission peak of hemoglobin substantially at wavenumber 1,109 cm$^{-1}$, wherein $S_3$ is proportional to an intensity of light within a band that contains substantially only blackbody radiation from surrounding portions of this apparatus and wherein a calculated concentration of blood late Maillard products is corrected by use of $S_2$ and $S_3$ to take into account effects due to changes in temperature of a containment vessel and blood volume intersected by the light from said source.

8. An apparatus as in claim 1 wherein said source of light is selected from the class consisting of a laser diode, a photodiode, a super-radiant photodiode, and a flash lamp.

9. An apparatus as in claim 1 wherein the light from said source is imaged through a wall of a contaminant vessel onto a region of the sample adjacent to the wall and said means for detecting light comprises at least one optical detector positioned such that each ray of emitted light that is received by said at least one optical detector travels along a substantially minimum length path from its point of emission to said at least one detector, whereby absorption of emitted light by the solution is substantially minimized as a function of the position of said at least one detector.

10. An apparatus as in claim 9 wherein the light from said source is imaged onto a region within the containment vessel and the light travels from said source to this region along a path that is substantially perpendicular to a wall of said containment vessel at a point that this light passes through such wall, whereby the amount of absorption of this light by components of the solution other than said selected component is substantially minimized.

11. An apparatus as in claim 9 wherein the light has an intensity of at least 5 Watts/cm$^2$ within the region in which the light is imaged.

12. An apparatus as in claim 9 wherein said containment vessel is an animal's body and the wall is the epidermis of such animal.

13. An apparatus as in claim 9 wherein said containment vessel is a finger of a human and the wall is the epidermis of this human.

14. An apparatus as in claim 9 further comprising:

temperature sensor means for measuring a temperature of a region from which light is received by said means for detecting; and means for maintaining a substantially constant, selected temperature T of those regions of said apparatus that emit blackbody radiation to said means for detecting.

15. An apparatus as in claim 14 wherein T is equal to 37° C.

16. An apparatus as in claim 1 further comprising:

a flat plate that is transparent to the emitted light, positioned such that light emitted from the sample of blood passes through this plate before reaching said means for detecting;

this plate providing a top surface against which a patient is to press a portion of the patient's epidermis during a blood test with this apparatus.

17. An apparatus as in claim 16 further comprising:

an optical fiber that penetrates through this flat plate and carries light from said source of light to said sample of blood;

said means for detecting is adjacent to this fiber and this plate.

18. An apparatus as in claim 16 further comprising:

an optical fiber that does not penetrate through said flat plate and which transports light from said source of light and directs this light through a portion of said flat plate at a point at which a patient is to press a portion of this patient's epidermis;

said means for detecting is adjacent to this fiber and this plate.

\* \* \* \* \*